US012077499B2

(12) United States Patent
Chadeayne

(10) Patent No.: US 12,077,499 B2
(45) Date of Patent: *Sep. 3, 2024

(54) CRYSTALLINE BIS-MIPROCIN FUMARATE

(71) Applicant: CAAMTECH, INC., Issaquah, WA (US)

(72) Inventor: Andrew R. Chadeayne, Issaquah, WA (US)

(73) Assignee: CAAMTECH, INC., Issaquah, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/317,169

(22) Filed: May 15, 2023

(65) Prior Publication Data

US 2023/0382859 A1 Nov. 30, 2023

Related U.S. Application Data

(63) Continuation of application No. 17/801,552, filed as application No. PCT/US2021/019893 on Feb. 26, 2021, now Pat. No. 11,780,808.

(60) Provisional application No. 62/982,441, filed on Feb. 27, 2020.

(51) Int. Cl.
*C07D 209/16* (2006.01)

(52) U.S. Cl.
CPC ........ *C07D 209/16* (2013.01); *C07B 2200/13* (2013.01)

(58) Field of Classification Search
CPC ................................... C07D 209/16
See application file for complete search history.

(56) References Cited

U.S. PATENT DOCUMENTS

| 2018/0221396 A1 | 8/2018 | Chadeayne |
| 2019/0142851 A1 | 5/2019 | Chadeayne |

OTHER PUBLICATIONS

Alzheimer's disease [online] retrieved from the internet on Mar. 25, 2022 URL https://www.mayoclinic.org/diseases-conditions/alzheimers-disease/symptoms-causes/syc-.*
Chen, et al. Amyloid beta:structure, biology and structure-based therapeutic development. Acta Pharmacologica Sinica 2017: 1205-1235.*
Cerebral palsy [online] retrieved from the internet on Dec. 6, 2023, URL https://www.mayoclinic.org/diseases-conditions/cerebral-palsy/symptoms-causes/syc-20353999?p=1.*
Mild cognitive impairment [online] retrieved from the internet on Dec. 6, 2023, URL https://www.mayoclinic.org/diseases-conditions/mild-cognitive-impairment/symptoms-causes/syc-20354578.*
Chistyakov et al., (2020) "The Polymorphism of Drugs: New Approaches to the Synthesis of Nanostructured Polymorphs," Pharmaceutics, 12, 34.

International Search Report and Written Opinion in International Application No. PCT/US2021/019893 dated Apr. 23, 2021.
Chadeayne et al., "The fumarate salts of the N-iso-propyl-N-methyl derivatives of DMT and psilocin", Crystallographic Communications, Sep. 2019.
Repke et al., "Psilocin analogs II. Synthesis of 3-[2-(dialkylamino)ethyl]-, 3-[2-(N-methyl-N-alkylamino)ethyl]-, and 3-[2-(cycloalkylamino)ethyl]indol-4-ols", Journal of Heterocyclic Chemistry, Jan. 1981, pp. 175-179, vol. 18(1).
Repke et al., "Psychotomimetic N-methyl-N-isopropyltryptamines. Effects of variation of aromatic oxygen substituents", 1985, Journal of Medicinal Chemistry, pp. 892-896, vol. 28(7).
International Preliminary Report on Patentability of PCT International Application No. PCT/US2021/019893, dated Aug. 30, 2022.
Cameron et al., Dark Classics in Chemical Neuroscience: N,N-Dimethyltryptamine (DMT), ACS Chemical Neuroscience; 2018, 9 pp. 2344-2357.
Carhart-Harris et al., "The Therapeutic Potential of Psychedelic Drugs: Past, Present, and Future"; Neuropsychopharmacology (2017) 42, pp. 2105-2113.
Chadeayne, et al., "The fumarate salds of the N-isopropyl-N-methyl derivatives of DMT and psilocin", Research Communications, Acta. Cryst. (2019), E75, pp. 1316-1320.
Dolomanov et al., "OLEX2: a complete structure solution, refinement and analysis program", J. Appl. Cryst. (2009), 42, pp. 339-341.
Etter et al., "Graph-Set Analysis of Hydrogen-Bond Patterns in Organic Crystals", Acta Cryst. (1990), B46, pp. 256-262.
Sheldrick, "Crystal structure refinement with SHELXL", Acta Cryst. (2015), C71, pp. 3-8.
Klein et al., "Investigation of the Structure—Activity Relationships of Psilocybin Analogues", ACS Pharmacol. Transl. Sci., 2021, 4, pp. 533-542.
Li et al., "Synthesis and Biological Activity of Novel 4-Tritamine-Memeric Compounds," Journal of Molecular Science (2015) vol. 31, issue 2.
Byrn et al., "Pharmaceutical Solids: A Strategic Approach to Regulatory Considerations", Pharma. Res., 12(7), pp. 945-954, 1995.
Caira, "Crystalline Polymorphism of Organic Compounds", Topics in Current Chemistry, 198, pp. 163-208, Jan. 1998 (1998).
Hilfiker et al., "Polymorphism in the Pharmaceutical Industry", Wile-VCH, 2006.
Brittain, "Polymorphism in Pharmaceutical Solids", Informa Healthcare, 2nd edition, 2009.
Stahl and Wermuth, "Handbook of Pharmaceutical Salts: Properties, Selection, and Use." Journal of Medicinal Chemistry, 2003.
Kumar et al., "An overview of automated systems relevant in pharmaceutical salt screening", Drug Discovery Today, 12(23-24), pp. 1046-1053, Dec. 2007 (Dec. 2007).
Serajuddin, "Salt formation to improve drug solubility", Advanced Drug Delivery Reviews, 59, pp. 603-616, May 2007 (May 2007).
Office Action in CA 3,169,033, dated Jan. 20, 2023.

(Continued)

*Primary Examiner* — Shawquia Jackson
(74) *Attorney, Agent, or Firm* — RAPHAEL BELLUM PLLC

(57) ABSTRACT

The disclosure relates to crystalline forms of bis(4-hydroxy-N-methyl-N-isopropyltryptammonium) fumarate ("crystalline bis-miprocin fumarate"), compositions containing that crystalline form, and their methods of treatment using them.

21 Claims, 5 Drawing Sheets

(56) References Cited

OTHER PUBLICATIONS

Johnson et al., "Potential Therapeutic Effects of Psilocybin", Neurotherapeutics (2017), 14, pp. 734-740.
Bastin, RJ et al. (2000) "Salt Selection and Optimisation for Pharmaceutical New Chemical Entities" Organic Process Research & Development, 4(5), 427-435.
Extended European Search Report in European Application No. EP21760087.3 dated Mar. 18, 2024.

\* cited by examiner

CRYSTALLINE BIS-MIPROCIN FUMARATE

CROSS-REFERENCE TO RELATED APPLICATIONS

This application is a continuation application of U.S. application Ser. No. 17/801,552, filed on Aug. 23, 2022; which is a 371 of PCT International Application No. PCT/US2021/019893, filed on Feb. 26, 2021; which claims priority to U.S. Provisional Application No. 62/982,441, filed on Feb. 27, 2020; the disclosures of which are all incorporated by reference.

TECHNICAL FIELD

This disclosure relates to crystalline bis(4-hydroxy-N-methyl-N-isopropyltryptammonium) fumarate, "crystalline bis-miprocin fumarate" and to pharmaceutical compositions containing crystalline bis-miprocin fumarate. Bis(4-hydroxy-N-methyl-N-isopropyltryptammonium) fumarate is itself a novel compound.

BACKGROUND

Psychoactive tryptamines have become a major area of study due to their potential for treating mood disorders including addiction, anxiety, depression, and PTSD (Johnson & Griffiths, 2017; Carhart-Harris & Goodwin, 2017). Recent reports also suggest that psychedelic microdosing can improve memory, attention, and sociability (Cameron, et al. 2020). The most studied of the psychoactive tryptamines is psilocybin, a naturally occurring tryptamines found in 'magic' mushrooms. Upon ingestion, psilocybin hydrolyzes to its active metabolite psilocin, which functions as a seratonin-2a agonist.

4-hydroxy-N-methyl-N-isopropyltryptamine (4-HO-MiPT), common name miprocin, is a psilocin analogue and a serotonergic psychedelic. Its synthesis was first reported in 1981 by Repke and co-worker (Repke, et al. 1981); its psychedelic effects were later described in collaboration with Alexander Shulgin (Repke, et al. 1985). The study suggests that the activity of miprocin is similar to psilocin. 4-substituted N,N-dialkyltryptamines, especially the 4-hydroxy tryptamines, act as $5\text{-}HT_{2A}$ receptor agonists (Klein et al. 2020, incorporated herein by reference). Psilocin and its homologues have higher efficacy and higher potency at $5\text{-}HT_{2A}$ (Klein et al. 2020). The first structure of 4-HO-MiPT was presented in 2019 (Chadeayne, Pham, et al. 2019a), which crystallizes as the hydrofumarate monohydrate. The reaction of this salt with lead (II) acetate generates the 4-hydroxy-N-methyl-N-isopropyltryptammonium/fumarate compound in a 2:1 ratio, which is a new salt.

Although therapeutic efficacy is the primary concern for an active pharmaceutical ingredient (API), the salt and solid-state form (i.e., the crystalline or amorphous form) of a drug candidate can be critical to its pharmacological properties, such as bioavailability, and to its development as a viable API. Recently, crystalline forms of API's have been used to alter the physicochemical properties of an API. Each crystalline form of a drug candidate can have different solid state (physical and chemical) properties. The differences in physical properties exhibited by a novel solid form of an API (such as a cocrystal or polymorph of the original therapeutic compound) affect pharmaceutical parameters such as storage stability, compressibility and density (important in formulation and product manufacturing), and solubility and dissolution rates (important factors in determining bioavailability). Because these practical physical properties are influenced by the solid-state properties of the crystalline form of the API, they can significantly impact the selection of a compound as an API, the ultimate pharmaceutical dosage form, the optimization of manufacturing processes, and absorption in the body. Moreover, finding the most adequate solid-state form for further drug development can reduce the time and the cost of that development.

Obtaining crystalline forms of an API is extremely useful in drug development. It permits better characterization of the drug candidate's chemical and physical properties. Crystalline forms often have better chemical and physical properties than the API in its amorphous state. Such crystalline forms may possess more favorable pharmaceutical and pharmacological properties or be easier to process.

SUMMARY

The disclosure relates to crystalline bis(4-hydroxy-N-methyl-N-isopropyltryptammonium) fumarate, "crystalline bis-miprocin fumarate" and to pharmaceutical compositions containing crystalline bis-miprocin fumarate. Bis(4-hydroxy-N-methyl-N-isopropyltryptammonium) fumarate is itself a novel compound.

In one embodiment, crystalline bis(4-hydroxy-N-methyl-N-isopropyltryptammonium) fumarate according to the disclosure is characterized by a monoclinic, C2lc crystal system space group at a temperature of about 200 K; unit cell dimensions a=19.770 (13) Å, b=9.477 (6) Å, c=17.620 (12) Å, and β=105.78 (2°).

The disclosure also relates to compositions comprising a crystalline bis-miprocin fumarate and to pharmaceutical compositions containing crystalline bis-miprocin fumarate and an excipient.

The disclosure also relates to compositions comprising a combination of, as a first component, a crystalline bis-miprocin fumarate and a second component selected from (a) a serotonergic drug, (b) a purified psilocybin derivative, (c) one or two purified cannabinoids and (d) a purified terpene.

The disclosure further relates to methods of preventing or treating a physical and/or psychological disorders comprising the step of administering to a subject in need thereof an effective amount of crystalline bis-miprocin fumarate and to pharmaceutical compositions containing a crystalline form of crystalline bis-miprocin fumarate, or a composition according to the disclosure.

The disclosure also relates to methods of preventing or treating inflammation and/or pain comprising the step of administering to a subject in need thereof an effective amount of crystalline bis-miprocin fumarate and to pharmaceutical compositions containing crystalline bis-miprocin fumarate, or a composition according to the disclosure.

DETAILED DESCRIPTION

Figure 1:
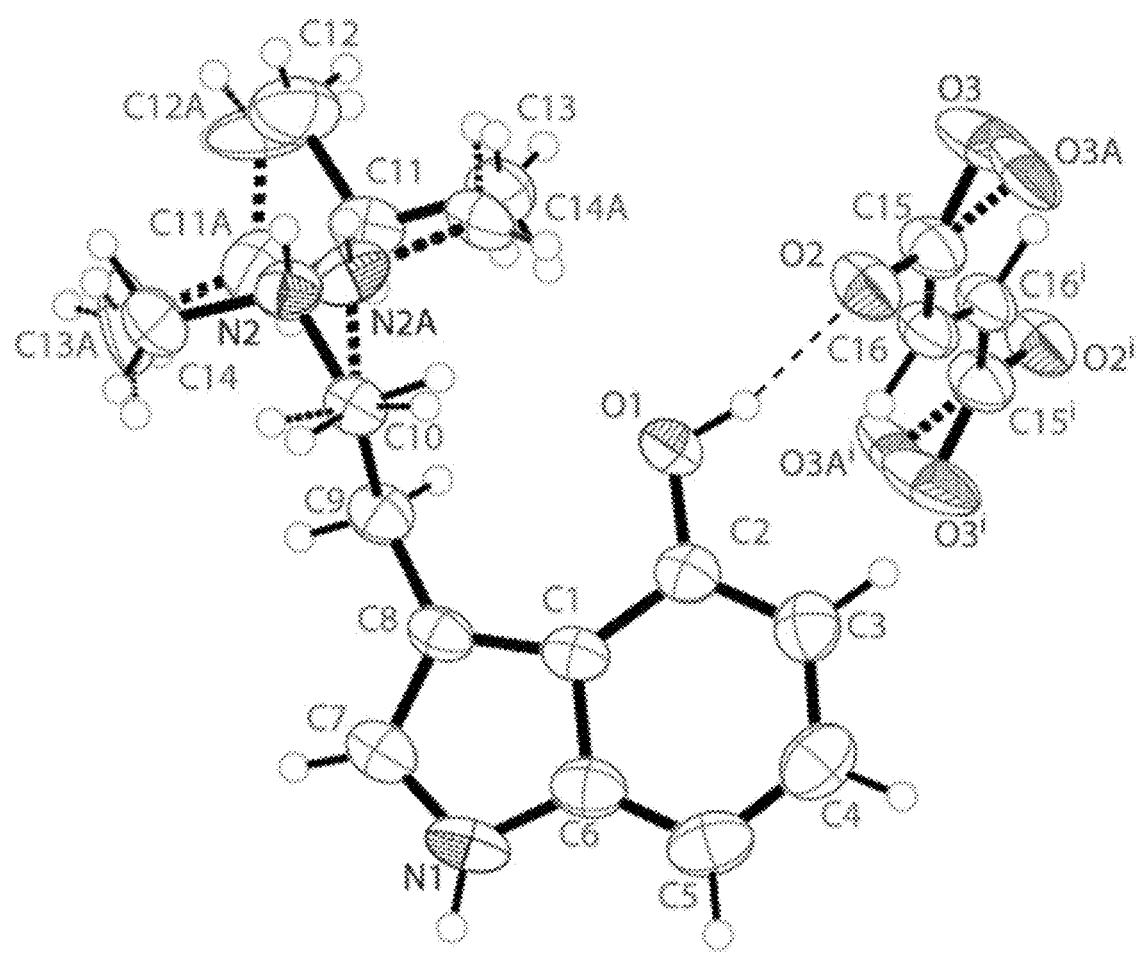
FIG. 1 shows the molecular structure of crystalline bis-miprocin fumarate.

This disclosure relates to crystalline bis(4-hydroxy-N-methyl-N-isopropyltryptammonium) fumarate ("crystalline bis-miprocin fumarate"), and to pharmaceutical compositions containing crystalline bis-miprocin fumarate according to the disclosure. The therapeutic uses of the crystalline bis-miprocin fumarate according to the disclosure, are described below as well as compositions containing them. The crystalline bis-miprocin fumarate according to the disclosure, and the methods used to characterize it are described below.

Bis(4-hydroxy-N-methyl-N-isopropyltryptammonium) fumarate ("bis-miprocin fumarate") is itself a novel compound having the following structural formula:

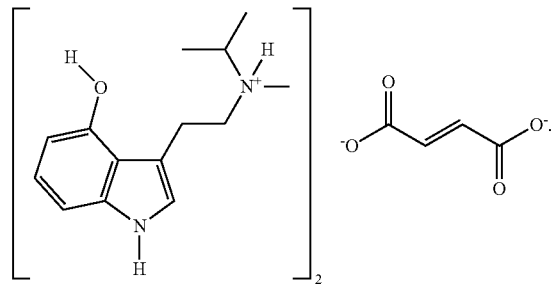

Methods of Treatment and Therapeutic Uses

In one embodiment, the crystalline bis-miprocin fumarate according to the disclosure, and the methods and the compositions—particularly the pharmaceutical compositions—of the disclosure are used to regulate the activity of a neurotransmitter receptor by administering a therapeutically effective dose of crystalline bis-miprocin fumarate of the disclosure. In another embodiment, the crystalline bis-miprocin fumarate according to the disclosure, and the methods and the compositions—particularly the pharmaceutical compositions—of the disclosure are used to treat inflammation and/or pain by administering a therapeutically effective dose of crystalline bis-miprocin fumarate of the disclosure.

Methods of the disclosure administer a therapeutically effective amount of crystalline bis-miprocin fumarate of the disclosure to prevent or treat a disease or condition, such as those discussed below for a subject in need of treatment. Crystalline bis-miprocin fumarate of the disclosure may be administered neat or as a composition comprising crystalline bis-miprocin fumarate of the disclosure as discussed below.

Crystalline bis-miprocin fumarate of the disclosure may be used to prevent and/or treat a psychological disorder. The disclosure provides a method for preventing and/or treating a psychological disorder by administering to a subject in need thereof a therapeutically effective amount of crystalline bis-miprocin fumarate of the disclosure, including the preferred embodiments discussed herein. The psychological disorder may be chosen from depression; psychotic disorder; schizophrenia; schizophreniform disorder (acute schizophrenic episode); schizoaffective disorder; bipolar I disorder (mania, manic disorder, manic-depressive psychosis); bipolar 11 disorder; major depressive disorder; major depressive disorder with psychotic feature (psychotic depression); delusional disorders (paranoia); Shared Psychotic Disorder (Shared paranoia disorder); Brief Psychotic disorder (Other and Unspecified Reactive Psychosis); Psychotic disorder not otherwise specified (Unspecified Psychosis); paranoid personality disorder; schizoid personality disorder; schizotypal personality disorder; anxiety disorder; social anxiety disorder; substance-induced anxiety disorder; selective mutism; panic disorder; panic attacks; agoraphobia; attention deficit syndrome, post-traumatic stress disorder (PTSD), premenstrual dysphoric disorder (PMDD), and premenstrual syndrome (PMS).

Crystalline bis-miprocin fumarate of the disclosure may be used to prevent and/or treat a brain disorder. The disclosure provides a method for preventing and/or treating a brain disorder by administering to a subject in need thereof a therapeutically effective amount of crystalline bis-miprocin fumarate of the disclosure, including the preferred embodiments discussed above. The brain disorder is chosen from Huntington's disease, Alzheimer's disease, dementia, and Parkinson's disease.

Crystalline bis-miprocin fumarate of the disclosure may be used to prevent and/or treat developmental disorders, delirium, dementia, amnestic disorders and other cognitive disorders, psychiatric disorders due to a somatic condition, drug-related disorders, schizophrenia and other psychotic disorders, mood disorders, anxiety disorders, somatoform disorders, factitious disorders, dissociative disorders, eating disorders, sleep disorders, impulse control disorders, adjustment disorders, or personality disorders. The disclosure provides a method for preventing and/or treating these disorders by administering to a subject in need thereof a therapeutically effective amount of crystalline bis-miprocin fumarate of the disclosure, including the preferred embodiments discussed above.

Crystalline bis-miprocin fumarate of the disclosure may be used to prevent and/or treat inflammation and/or pain, such as for example inflammation and/or pain associated with inflammatory skeletal or muscular diseases or conditions. The disclosure provides a method for preventing and/or treating an inflammation and/or pain by administering to a subject in need thereof a therapeutically effective amount of crystalline bis-miprocin fumarate of the disclosure, including the preferred embodiments discussed herein. Generally speaking, treatable "pain" includes nociceptive, neuropathic, and mix-type. A method of the disclosure may reduce or alleviate the symptoms associated with inflammation, including but not limited to treating localized manifestation of inflammation characterized by acute or chronic swelling, pain, redness, increased temperature, or loss of function in some cases. A method of the disclosure may reduce or alleviate the symptoms of pain regardless of the cause of the pain, including but not limited to reducing pain of varying severity, i.e., mild, moderate and severe pain, acute pain and chronic pain. A method of the disclosure is effective in treating joint pain, muscle pain, tendon pain, burn pain, and pain caused by inflammation such as rheumatoid arthritis. Skeletal or muscular diseases or conditions which may be treated include but are not limited to musculoskeletal sprains, musculoskeletal strains, tendinopathy, peripheral radiculopathy, osteoarthritis, joint degenerative disease, polymyalgia rheumatica, juvenile arthritis, gout, ankylosing spondylitis, psoriatic arthritis, systemic lupus erythematosus, costochondritis, tendonitis, bursitis, such as the common lateral epicondylitis (tennis elbow), medial epicondylitis (pitchers elbow) and trochanteric bursitis, temporomandibular joint syndrome, and fibromyalgia.

Compositions

The disclosure also relates to compositions comprising an effective amount of crystalline bis-miprocin fumarate of the disclosure, especially pharmaceutical compositions comprising a therapeutically effective amount of crystalline bis-miprocin fumarate of the disclosure and a pharmaceutically acceptable carrier (also known as a pharmaceutically acceptable excipient). As discussed above, the crystalline bis-miprocin fumarate of the disclosure may be, for example, therapeutically useful to prevent and/or treat the psychological and other disorders discussed above.

A composition or a pharmaceutical composition of the disclosure may be in any form which contains the crystalline bis-miprocin fumarate of the disclosure. The composition may be, for example, a tablet, capsule, liquid suspension, injectable, topical, or transdermal. The compositions or pharmaceutical compositions generally contain, for example, about 1% to about 99% by weight of crystalline bis-miprocin fumarate of the disclosure and, for example, 99% to 1% by weight of at least one suitable pharmaceutical excipient. In one embodiment, the composition may be between about 5% and about 75% by weight of crystalline bis-miprocin fumarate of the disclosure with the rest being at least one suitable pharmaceutical excipient or at least one other adjuvant, as discussed below.

Published US applications US 2018/0221396 A1 and US 2019/0142851 A1 disclose compositions comprising a combination of a first purified psilocybin derivative with a second purified psilocybin derivative, with one or two purified cannabinoids or with a purified terpene. Various ratios of these components in the composition are also disclosed. The disclosures of US 2018/0221396 A1 and US 2019/0142851 A1 are incorporated herein by reference. According to this disclosure, crystalline bis-miprocin fumarate of the disclosure may be used as the "first purified psilocybin derivative" in the compositions described in US 2018/0221396 A1 and US 2019/0142851 A1. Accordingly, this disclosure provides a composition comprising as a first component: crystalline bis-miprocin fumarate of the disclosure; and as a second component selected from (a) a serotonergic drug, (b) a purified psilocybin derivative, (c) one or two purified cannabinoids and (d) a purified terpene; with the rest being at least one suitable pharmaceutical excipient or at least one other adjuvant, as discussed below. Such a composition may be a pharmaceutical composition wherein the components are present individually in therapeutically effective amounts or by combination in a therapeutically effective amount to treat a disease, disorder, or condition as described herein. A serotonergic drug refers to a compound that binds to, blocks, or otherwise influences (e.g., via an allosteric reaction) activity at a serotonin receptor as described in US 2018/0221396 A1 and [0305]-[0311] US 2019/0142851 A1 as well as the disclosed preferred embodiments, incorporated here by reference. Exemplary psilocybin derivatives include but are not limited to psilocybin itself and the psilocybin derivates described in US 2018/0221396 A1 and [082]-[0110] US 2019/0142851 A1 as well as the disclosed preferred embodiments. Exemplary cannabinoids include but are not limited to the cannabinoids described in US 2018/0221396 A1 and [0112]-[0160] US 2019/0142851 A1 as well as the disclosed preferred embodiments. Exemplary terpenes include but are not limited to the terpenes described in US 2018/0221396 A1 and [0161]-[0300] US 2019/0142851 A1 as well as the disclosed preferred embodiments.

A pharmaceutical formulation of the disclosure may comprise, consist essentially of, or consist of (a) crystalline bis-miprocin fumarate and (b) a second active compound selected from a serotonergic drug, a purified psilocybin derivative, a purified cannabinoid, or a purified terpene and (c) a pharmaceutically acceptable excipient. The crystalline bis-miprocin fumarate and the second active compound are each present in a therapeutically effective amount using a purposefully engineered and unnaturally occurring molar ratios. Exemplary molar ratios of the crystalline bis-miprocin fumarate to the second active compound in a composition of the disclosure include but are not limited to from about 0.1:100 to about 100:01, from about 1:100 to about 100:1, from about 1:50 to about 50:1, from about 1:25 to about 25:1, from about 1:20 to about 20:1, from about 1:10 to about 10:1, from about 1:5 to about 5:1, from about 1:2 to about 2:1 or may be about 1:1.

A pharmaceutical formulation of the disclosure may comprise a composition of the disclosure and a serotonergic drug, a purified psilocybin derivative, a purified cannabinoid, or a purified terpene, each present in a therapeutically effective amount using a purposefully engineered and unnaturally occurring molar ratios. Published US applications US 2018/0221396 A1 and US 2019/0142851 A1 disclose compositions comprising a combination of a purified psilocybin derivative with a second purified psilocybin derivative, with one or two purified cannabinoids or with a purified terpene. The disclosures of US 2018/0221396 A1 and US 2019/0142851 A1 are incorporated herein by reference. According to this disclosure composition containing crystalline bis-miprocin fumarate as discussed above may be used in place of a "purified psilocybin derivative" in the compositions described in US 2018/0221396 A1 and US 2019/0142851 A1. Accordingly, the disclosure provides a pharmaceutical formulation comprising as (a) crystalline bis-miprocin fumarate and as a second component selected from (a) a purified psilocybin derivative, (b) one or two purified cannabinoids and (c) a purified terpene; with the rest being at least one suitable pharmaceutical excipient or at least one other adjuvant, as discussed below. Such a composition may be a pharmaceutical composition wherein the components are present individually in therapeutic effective amounts or by combination in a therapeutically effective amount to treat a disease, disorder, or condition as described herein.

A serotonergic drug refers to a compound that binds to, blocks, or otherwise influences (e.g., via an allosteric reaction) activity at a serotonin receptor as described in US 2018/0221396 A1 and [0305]-[0311] US 2019/0142851 A1 as well as the disclosed preferred embodiments, incorporated here by reference. Some exemplary serotonergic drugs include the following molecules: 6-Allyl-N,N-diethyl-NL, N,N-Dibutyl-T, N,N-Diethyl-T, N,N-Diisopropyl-T, 5-Methoxy-alpha-methyl-T, N,N-Dimethyl-T, 2,alpha-Dimethyl-T, alpha,N-Dimethyl-T, N,N-Dipropyl-T, N-Ethyl-N-isopropyl-T, alpha-Ethyl-T, 6,N,N-Triethyl-NL, 3,4-Dihydro-7-methoxy-1-methyl-C, 7-Methyoxy-1-methyl-C, N,N-Dibutyl-4-hydroxy-T, N,N-Diethyl-4-hydroxy-T, N,N-Diisopropyl-4-hydroxy-T, N,N-Dimethyl-4-hydroxy-T, N,N-Dimethyl-5-hydroxy-T, N, N-Dipropyl-4-hydroxy-T, N-Ethyl-4-hydroxy-N-methyl-T, 4-Hydroxy-N-isopropyl-N-methyl-T, 4-Hydroxy-N-methyl-N-propyl-T, 4-Hydroxy-N,N-tetramethylene-T Ibogaine, N,N-Diethyl-L, N-Butyl-N-methyl-T, N,N-Diisopropyl-4,5-methylenedioxy-T, N,N-Diisopropyl-5,6-methylenedioxy-T, N,N-Dimethyl-4,5-methylenedioxy-T, N,N-Dimethyl-5,6-methylenedioxy-T, N-Isopropyl-N-methyl-5,6-methylenedioxy-T, N,N-Diethyl-2-methyl-T, 2,N,N-Trimethyl-T, N-Acetyl-5-methoxy-T, N,N-Diethyl-5-methoxy-T, N,N-Diisopropyl-5- methoxy-T, 5-Methoxy-N,N-dimethyl-T, N-Isopropyl-4-methoxy-N-methyl-T, N-Isopropyl-5-methoxy-N-methyl-T, 5,6-Dimethoxy-N-isopropyl-N-methyl-T, 5-Methoxy-N-methyl-T, 5-Methoxy-N,N-tetramethylene-T, 6-Methoxy-1-methyl-1,2,3,4-tetrahydro-C, 5-Methoxy-2,N,N-trimethyl-T, N,N-Dimethyl-5-methylthio-T, N-Isopropyl-N-methyl-T, alpha-Methyl-T, N-Ethyl-T, N-Methyl-T, 6-Propyl-N L, N,N-Tetramethylene-T, Tryptamine, and 7-Methoxy-1-methyl-1,2,3,4-tetrahydro-C, alpha,N-Dimethyl-5-methoxy-T. For additional information regarding these compounds See Shulgin, A. T., & Shulgin, A. (2016). Tihkal: The Continuation. Berkeley, Calif.: Transform Press. In one embodiment, a serotonergic drug is chosen from alprazolam, amphetamine, aripiprazole, azapirone, a barbiturate, bromazepam, bupropion, buspirone, a cannabinoid, chlordiazepoxide, citalopram, clonazepam, clorazepate, dextromethorphan, diazepam, duloxetine, escitalopram, fluoxetine, flurazepam, fluvoxamine, lorazepam, lysergic acid diethylamide, lysergamide, 3,4-methylenedioxymethamphetamine, milnacipran, mirtazapine, naratriptan, paroxetine, pethidine, phenethylamine, psicaine, oxazepam, reboxetine, serenic, serotonin, sertraline, temazepam, tramadol, triazolam, a tryptamine, venlafaxine, vortioxetine, and/or derivatives thereof.

Exemplary psilocybin derivatives include but are not limited to psilocybin itself and the psilocybin derivates described in US 2018/0221396 A1 and [082]-[0110] US 2019/0142851 A1 as well as the disclosed preferred embodiments, incorporated here by reference. In one embodiment, the compositions disclosed herein comprise one or more purified psilocybin derivatives chosen from: [3-(2-Dimethylaminoethyl)-1H-indol-4-yl] dihydrogen phosphate, 4-hydroxytryptamine, 4-hydroxy-N,N-dimethyltryptamine, [3-(2-methylaminoethyl)-1H-indol-4-yl]dihydrogen phosphate, 4-hydroxy-N-methyltryptamine, [3-(aminoethyl)-1H-indol-4-yl] dihydrogen phosphate, [3-(2-trimethylaminoethyl)-1H-indol-4-yl] dihydrogen phosphate, and 4-hydroxy-N,N,N-trimethyltryptamine.

Exemplary cannabinoids include but are not limited to the cannabinoids described in US 2018/0221396 A1 and [0112]-[0160] US 2019/0142851 A1 as well as the disclosed preferred embodiments, incorporated here by reference. Examples of cannabinoids within the context of this disclosure include the following molecules: cannabichromene (CBC), cannabichromenic acid (CBCA), cannabichromevarin (CBCV), cannabichromevarinic acid (CBCVA), cannabicyclol (CBL), cannabicyclolic acid (CBLA), cannabicyclovarin (CBLV), cannabidiol (CBD), cannabidiol monomethylether (CBDM), cannabidiolic acid (CBDA), cannabidiorcol (CBD-C1), cannabidivarin (CBDV), cannabidivarinic acid (CBDVA), cannabielsoic acid B (CBEA-B), cannabielsoin (CBE), cannabielsoin acid A (CBEA-A), cannabigerol (CBG), cannabigerol monomethylether (CBGM), cannabigerolic acid (CBGA), Cannabigerolic acid monomethylether (CBGAM), cannabigerovarin (CBGV), cannabigerovarinic acid (CBGVA), cannabinodiol (CBND), cannabinodivarin (CBDV), cannabinol (CBN), cannabinol methylether (CBNM), cannabinol-C2 (CBN-C2), cannabinol-C4 (CBN-C4), cannabinolic acid (CBNA), cannabiorcool (CBN-C1), cannabivarin (CBV), cannabitriol (CBT), cannabitriolvarin (CBTV), 10-ethoxy-9-hydroxy-delta-6a-tetrahydrocannabinol, cannbicitran (CBT), cannabiripsol (CBR), 8,9-dihydroxy-delta-6a-tetrahydrocannabinol, delta-8-tetrahydrocannabinol (A8-THC), delta-8-tetrahydrocannabinolic acid (A8-THCA), delta-9-tetrahydrocannabinol (THC), delta-9-tetrahydrocannabinol-C4 (THC-C4), delta-9-tetrahydrocannabinolic acid A (THCA-A), delta-9-tetrahydrocannabinolic acid B (THCA-B), delta-9-tetrahydrocannabinolic acid-C4 (THCA-C4), delta-9-tetrahydrocannabiorcol (THC-C1), delta-9-tetrahydrocannabiorcolic acid (THCA-C1), delta-9-tetrahydrocannabivarin (THCV), delta-9-tetrahydrocannabivarinic acid (THCVA), 10-oxo-delta-6a-tetrahydrocannabinol (OTHC), cannabichromanon (CBCF), cannabifuran (CBF), cannabiglendol, delta-9-cis-tetrahydrocannabinol (cis-THC), tryhydroxy-delta-9-tetrahydrocannabinol (triOH-THC), dehydrocannabifuran (DCBF), and 3,4,5,6-tetrahydro-7-hydroxy-alpha-alpha-2-trimethyl-9-n-propyl-2,6-metha-no-2H-1-benzoxocin-5-methanol.

In one embodiment, the purified cannabinoid is chosen from THC, THCA, THCV, THCVA, CBC, CBCA, CBCV, CBCVA, CBD, CBDA, CBDV, CBDVA, CBG, CBGA, CBGV, or CBGVA.

Exemplary terpenes include but are not limited to the terpenes described in US 2018/0221396 A1 and [0161]-[0300] US 2019/0142851 A1 as well as the disclosed preferred embodiments, incorporated here by reference. In one embodiment, a purified terpene is chosen from acetanisole, acetyl cedrene, anethole, anisole, benzaldehyde, bornyl acetate, borneol, cadinene, cafestol, caffeic acid, camphene, camphor, capsaicin, carene, carotene, carvacrol, carvone, caryophyllene, caryophyllene, caryophyllene oxide, cedrene, cedrene epoxide, cecanal, cedrol, cembrene, cinnamaldehyde, cinnamic acid, citronellal, citronellol, cymene, eicosane, elemene, estragole, ethyl acetate, ethyl cinnamate, ethyl maltol, eucalyptol/1,8-cineole, eudesmol, eugenol, euphol, farnesene, farnesol, fenchone, geraniol, geranyl acetate, guaia-1(10),11-diene, guaiacol, guaiol, guaiene, gurjunene, herniarin, hexanaldehyde, hexanoic acid, humulene, ionone, ipsdienol, isoamyl acetate, isoamyl alcohol, isoamyl formate, isoborneol, isomyrcenol, isoprene, isopulegol, isovaleric acid, lavandulol, limonene, gamma-linolenic acid, linalool, longifolene, lycopene, menthol, methyl butyrate, 3-mercapto-2-methylpentanal, beta-mercaptoethanol, mercaptoacetic acid, methyl salicylate, methylbutenol, methyl-2-methylvalerate, methyl thiobutyrate, myrcene, gamma-muurolene, nepetalactone, nerol, nerolidol, neryl acetate, nonanaldehyde, nonanoic acid, ocimene, octanal, octanoic acid, pentyl butyrate, phellandrene, phenylacetaldehyde, phenylacetic acid, phenylethanethiol, phytol, pinene, propanethiol, pristimerin, pulegone, retinol, rutin, sabinene, squalene, taxadiene, terpineol, terpine-4-ol, terpinolene, thujone, thymol, umbelliferone, undecanal, verdoxan, or vanillin. In one embodiment, a purified terpene is chosen from bornyl acetate, alpha-bisabolol, borneol, camphene, camphor, carene, caryophyllene, cedrene, cymene, elemene, eucalyptol, eudesmol, farnesene, fenchol, geraniol, guaiacol, humulene, isoborneol, limonene, linalool, menthol, myrcene, nerolidol, ocimene, phellandrene, phytol, pinene, pulegone, sabinene, terpineol, terpinolene, or valencene.

Exemplary compositions of crystalline bis-miprocin fumarate and a second compound selected from a serotonergic drug, a purified psilocybin derivative, a purified cannabinoid, or a purified terpene in exemplary molar ratios are shown in Table 1.

TABLE 1

| Second Compound | Molar ratio of crystalline bis-miprocin fumarate: second compound | Molar ratio of crystalline bis-miprocin fumarate: second compound | Molar ratio of crystalline bis-miprocin fumarate: second compound |
| --- | --- | --- | --- |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-12-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |

Exemplary pharmaceutical compositions of crystalline bis-miprocin fumarate and a second compound selected from a serotonergic drug, a purified psilocybin derivative, a purified cannabinoid, or a purified terpene and an excipient with exemplary molar ratios of crystalline bis-miprocin fumarate to the second compound are shown in Table 2.

TABLE 2

| Second Compound | Molar ratio of crystalline bis-miprocin fumarate: second compound | Molar ratio of crystalline bis-miprocin fumarate: second compound | Molar ratio of crystalline bis-miprocin fumarate: second compound |
| --- | --- | --- | --- |
| Citalopram | About 1:100 to about 100:1 | About 1:25 to about 25:1 | About 1:5 to about 5:1 |
| Escitalopram | About 1:100 to about 100:1 | About 1:25 to about 25:1 | About 1:5 to about 5:1 |
| Fluoxetine | About 1:100 to about 100:1 | About 1:25 to about 25:1 | About 1:5 to about 5:1 |

TABLE 2-continued

| Second Compound | Molar ratio of crystalline bis-miprocin fumarate: second compound | Molar ratio of crystalline bis-miprocin fumarate: second compound | Molar ratio of crystalline bis-miprocin fumarate: second compound |
|---|---|---|---|
| Paroxetine | About 1:100 to about 100:1 | About 1:25 to about 25:1 | About 1:5 to about 5:1 |
| Sertraline | About 1:100 to about 100:1 | About 1:25 to about 25:1 | About 1:5 to about 5:1 |
| [3-(2-Dimethylaminoethyl)-1H-indol-4-yl] dihydrogen phosphate | About 1:100 to about 100:1 | About 1:25 to about 25:1 | About 1:5 to about 5:1 |
| 4-hydroxytryptamine | About 1:100 to about 100:1 | About 1:25 to about 25:1 | About 1:5 to about 5:1 |
| 4-hydroxy-N,N-dimethyltryptamine | About 1:100 to about 100:1 | About 1:25 to about 25:1 | About 1:5 to about 5:1 |
| [3-(2-methylaminoethyl)-1H-indol-4-yl] dihydrogen phosphate | About 1:100 to about 100:1 | About 1:25 to about 25:1 | About 1:5 to about 5:1 |
| 4-hydroxy-N-methyltryptamine | About 1:100 to about 100:1 | About 1:25 to about 25:1 | About 1:5 to about 5:1 |
| [3-(aminoethyl)-1H-indol-4-yl] dihydrogen phosphate | About 1:100 to about 100:1 | About 1:25 to about 25:1 | About 1:5 to about 5:1 |
| [3-(2-trimethylaminoethyl)-1H-indol-4-yl] dihydrogen phosphate | About 1:100 to about 100:1 | About 1:25 to about 25:1 | About 1:5 to about 5:1 |
| 4-hydroxy-N,N,N-trimethyltryptamine | About 1:100 to about 100:1 | About 1:25 to about 25:1 | About 1:5 to about 5:1 |
| THC | About 1:100 to about 100:1 | About 1:25 to about 25:1 | About 1:5 to about 5:1 |
| CBC | About 1:100 to about 100:1 | About 1:25 to about 25:1 | About 1:5 to about 5:1 |
| CBD | About 1:100 to about 100:1 | About 1:25 to about 25:1 | About 1:5 to about 5:1 |
| CBG | About 1:100 to about 100:1 | About 1:25 to about 25:1 | About 1:5 to about 5:1 |
| Myrcene | About 1:100 to about 100:1 | About 1:25 to about 25:1 | About 1:5 to about 5:1 |
| Pinene | About 1:100 to about 100:1 | About 1:25 to about 25:1 | About 1:5 to about 5:1 |
| Caryophyllene | About 1:100 to about 100:1 | About 1:25 to about 25:1 | About 1:5 to about 5:1 |
| Limonene | About 1:100 to about 100:1 | About 1:25 to about 25:1 | About 1:5 to about 5:1 |
| Humulene | About 1:100 to about 100:1 | About 1:25 to about 25:1 | About 1:5 to about 5:1 |
| Linalool | About 1:100 to about 100:1 | About 1:25 to about 25:1 | About 1:5 to about 5:1 |

An "effective amount" or a "therapeutically effective amount" of crystalline bis-miprocin fumarate according to the disclosure is generally in the range of about 0.1 to about 100 mg daily (oral dose), of about 0.1 to about 50 mg daily (oral dose) of about 0.25 to about 25 mg daily (oral dose), of about 0.1 to about 5 mg daily (oral dose) or of about 0.5 to about 2.5 mg daily (oral dose). The actual amount required for treatment of any particular patient may depend upon a variety of factors including, for example, the disease being treated and its severity; the specific pharmaceutical composition employed; the age, body weight, general health, sex, and diet of the patient; the mode of administration; the time of administration; the route of administration; and the rate of excretion; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. Crystalline bis-miprocin fumarate according to the disclosure, compositions and pharmaceutical compositions containing it may be used in combination with other agents that are generally administered to a patient being treated for psychological and other disorders discussed above. They may also be co-formulated with one or more of such agents in a single pharmaceutical composition.

Depending on the type of composition or pharmaceutical composition, the excipient or pharmaceutically acceptable carrier may be chosen from any one or a combination of carriers known in the art. The choice of the pharmaceutically acceptable carrier depends upon the pharmaceutical form and the desired method of administration to be used. Preferred carriers include those that do not substantially alter the crystalline form of miprocin or produce undesirable biological effects or otherwise interact in a deleterious manner with any other component(s) of the pharmaceutical composition.

The compositions or pharmaceutical compositions of the disclosure may be prepared by methods known in the pharmaceutical formulation art, for example, see Remington's Pharmaceutical Sciences, 18th Ed., (Mack Publishing Company, Easton, Pa., 1990), which is incorporated herein by reference. In a solid dosage form, the crystalline form of miprocin may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alginates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Excipients or pharmaceutically acceptable adjuvants known in the formulation art may also be used in the pharmaceutical compositions of the disclosure. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a composition or a pharmaceutical composition of the disclosure may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier).

Administration of crystalline bis-miprocin fumarate of the disclosure in pure form, with a permeation enhancer, with stabilizers (e.g., antioxidants), or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, liquid dosage forms, such as, for example, tablets, suppositories, pills, soft elastic and hard gelatin capsules, powders, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

Examples

The preparation of crystalline bis-miprocin fumarate is described below.

Synthesis and Crystallization 61.2 mg of 4-HO-MiPT fumarate was dissolved in 10 mL of deionized water. 29.3 mg of lead (II) acetate was dissolved in 2 mL of deionized water and then added to the tryptamine solution. After sonication, a white precipitate formed. The powder was removed via vacuum filtration. The solvent was removed from the resulting solution in vacuo to yield a sticky powder. The powder was recrystallized in methanol to yield single crystals suitable for X-ray diffraction.

Single crystal data, data collection, and structure refinement details are summarized in Table 3. The data for crystalline bis-miprocin fumarate in Table 3 relates to the asymmetric unit.

TABLE 3

| | Bis-miprocin fumarate |
|---|---|
| Chemical formula | $C_{14}H_{21}N_2O \cdot C_2HO_2$ |
| $M_r$ | 290.54 |
| Crystal system, space group | Monoclinic, C2/c |
| Temperature (K) | 200 |
| a, b, c (Å) | 19.770 (13), 9.477 (6), 17.620 (12) |
| β (°) | 105.78 (2) |
| V(Å$^3$) | 3177 (4) |
| Z | 8 |
| F(000) | 1249 |
| $D_x$ (Mg m$^{-3}$) | 1.215 |
| Radiation type | $M_o K_\alpha$ |
| λ (Å) | 0.71073 |
| μ (mm$^{-1}$) | 0.08 |
| Crystal size (mm) | 0.25 × 0.2 × 0.1 |
| Diffractometer | Bruker D8 CMOS |
| Absorption correction | Multi-scan SADABS2016/2 (Bruker, 2016) was used for absorption correction. wR2(int) was 0.0666 before and 0.0618 after correction. The Ratio of minimum to maximum transmission is 0.9289. The λ/2 correction factor is not present. |
| $T_{min}$, $T_{max}$ | 0.692, 0.745 |
| No. of measured, independent and observed [I > 2σ(I)] reflections | 39417, 2890, 2007 |
| $R_{int}$ | 0.086 |
| $\theta_{max}$, $\theta_{min}$ (°) | 25.5, 2.6 |
| R[F$^2$ > 2σ(F$^2$)], wR(F$^2$), S | 0.049, 0.113, 1.05 |
| w | $1/[\sigma^2(F_o^2) + (0.0355P)^2 + 2.9538P]$ where $P = (F_o^2 + 2F_c^2)/3$ |
| No. of reflections | 2890 |
| No. of parameters | 250 |
| No. of restraints | 4 |
| h, k, l | −23→23, −11→11, −21→21 |

TABLE 3-continued

| | Bis-miprocin fumarate |
|---|---|
| H-site location | mixed |
| H-atom treatment | H atoms treated by a mixture of independent and constrained refinement |
| $(\Delta/\sigma)_{max}$ | <0.001 |
| $\Delta\rho_{max}, \Delta\rho_{min}$ (e Å$^{-3}$) | 0.15, −0.14 |
| Extinction Correction | SHELXL2018 (Sheldrick, 2018), Fc* = kFc[1 + 0.001 × Fc$^2$λ$^3$/sin(2θ)]$^{-1/4}$ |
| Extinction Coefficient | 0.0039 (5) |

Cell refinement: SAINT V8.38A (Bruker, 2018); data reduction: SAINT V8.38A (Bruker, 2018); program(s) used to solve structure: SHELXT 2014/5 (Sheldrick, 2014); program(s) used to refine structure: SHELXL 2018/3 (Sheldrick, 2015); molecular graphics: Olex2 1.3 (Dolomanov et al., 2009); software used to prepare material for publication: Olex2 1.3 (Dolomanov et al., 2009).

The molecular structure of crystalline bis-miprocin fumarate, showing the atom labeling, is shown in FIG. 1. Hydrogen bonds are shown as dashed lines.

Crystalline bis-miprocin fumarate has a protonated tryptammonium cation and one half of a fumarate dianion in the asymmetric unit. The tryptammonium and fumarate ions are held together in one dimensional chains by N—H . . . O and O—H . . . O hydrogen bonds. These chains are a combination of $R^2_4$ (20) rings, $C^2_2$ (15) and $C^4_4$ (30) parallel chains along (110). These chains are further adjoined by N—H . . . π interactions. The cation possesses a near planar indole, with mean deviation from planarity of 0.014 Å.

The N-methyl-N-isopropylammonium group is disordered over two orientations with a 0.758 (7):0.242 (7) ratio. The half fumarate anion is also disordered over two positions in the same ratio. The fumarate dianion is in the trans configuration and is slightly distorted from planarity with r.m.s. deviations of 0.021 Å and 0.073 Å for the two configurations.

Figure 2:
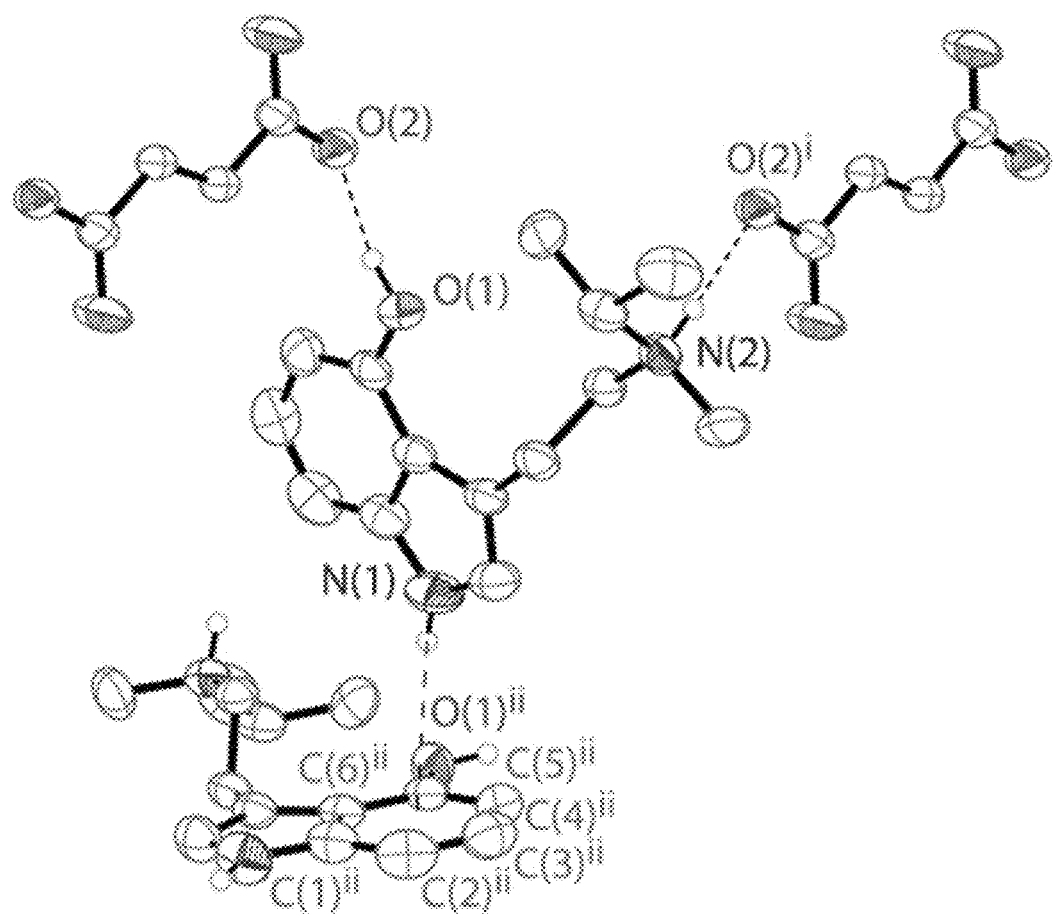
FIG. 2 shows the hydrogen bonding of the tryptammonium cation in the structure of the crystalline bis-miprocin fumarate.

The hydrogen bonding of the tryptammonium cation in the structure of the crystalline bis-miprocin fumarate is shown in FIG. 2. Hydrogen bonds shown as dashed lines. The ions are further linked through N—H . . . π interactions between the indole N—H and the aromatic ring of the indole of another tryptammonium ion, as shown in FIG. 2.

Figure 3:
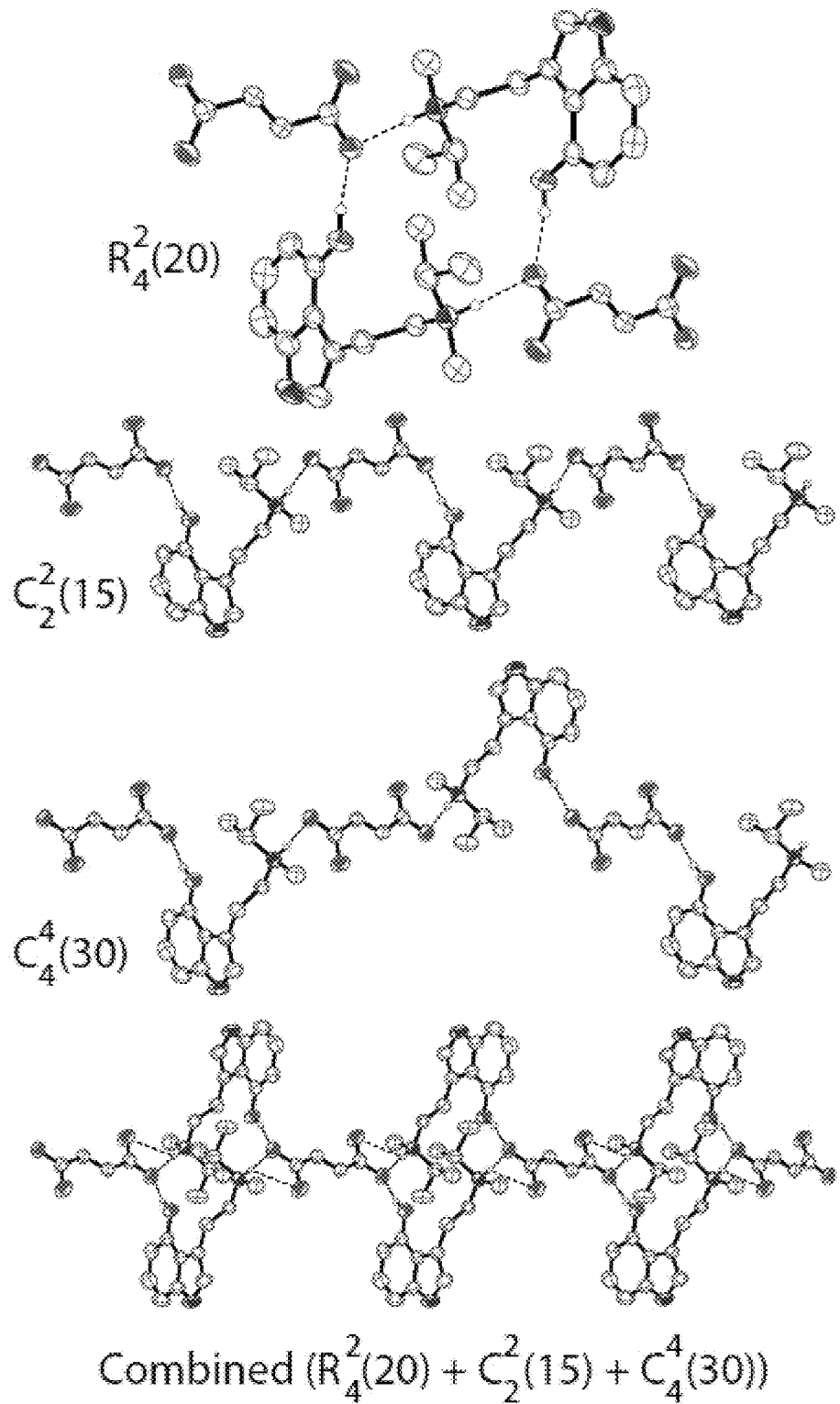
FIG. 3 shows the chains and rings of the two tryptammonium cations and two fumarate anions joined together.

Two tryptammonium cations and two fumarate anions join together through N—H . . . O and O—H . . . O hydrogen bonds to form rings with graph-set notation $R^2_4$ (20) (Etter, et al. 1990). The rings are joined together by two parallel chains along (110). These chains have graph-set notation $C^2_2$ (15) and $C^4_4$ (30). The chains and rings are shown in FIG. 3.

Figure 4:
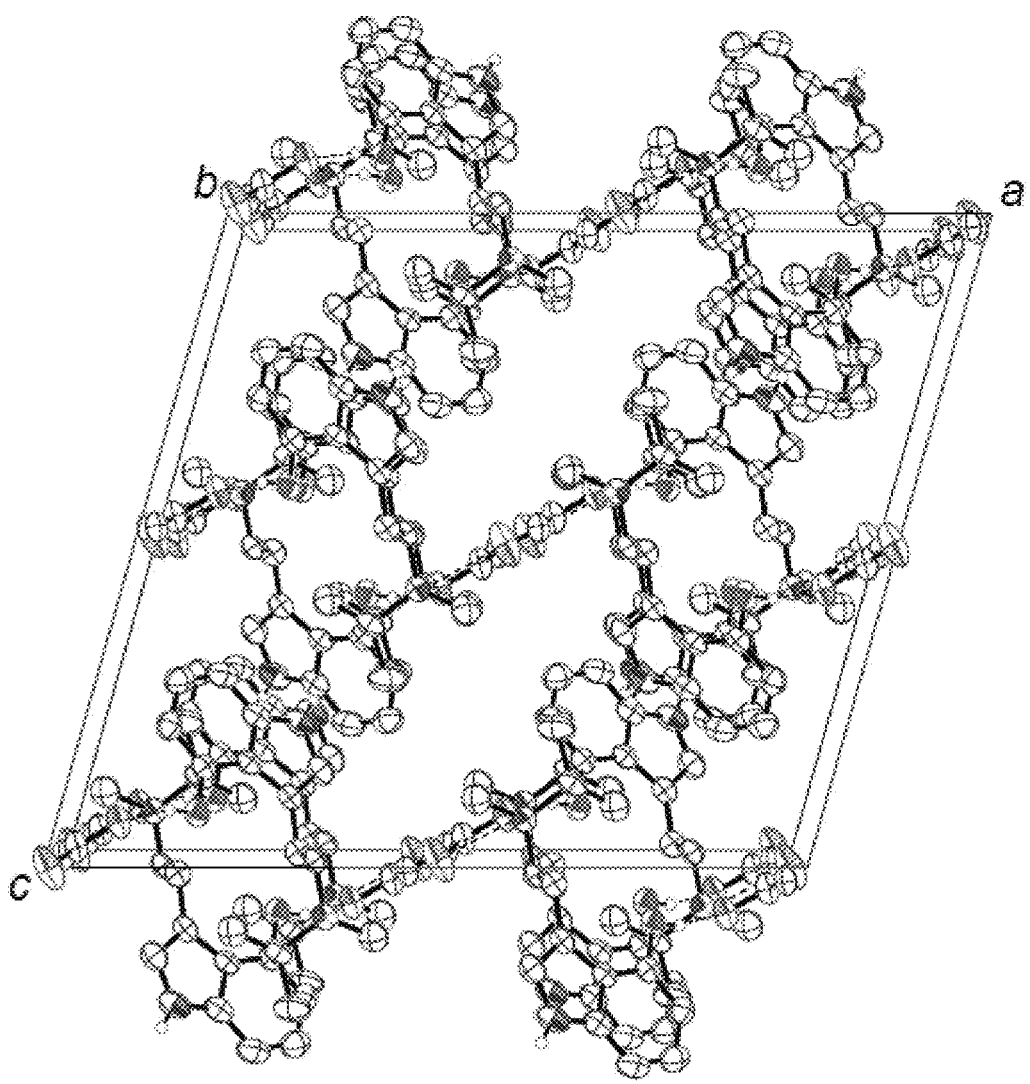
FIG. 4 shows the crystal packing of crystalline bis-miprocin fumarate, viewed along the b-axis.

The crystal packing of crystalline bis-miprocin fumarate, viewed along the b-axis, is shown in FIG. 4. The N—H . . . O and O—H . . . O hydrogen bonds are shown as dashed lines.

Figure 5:
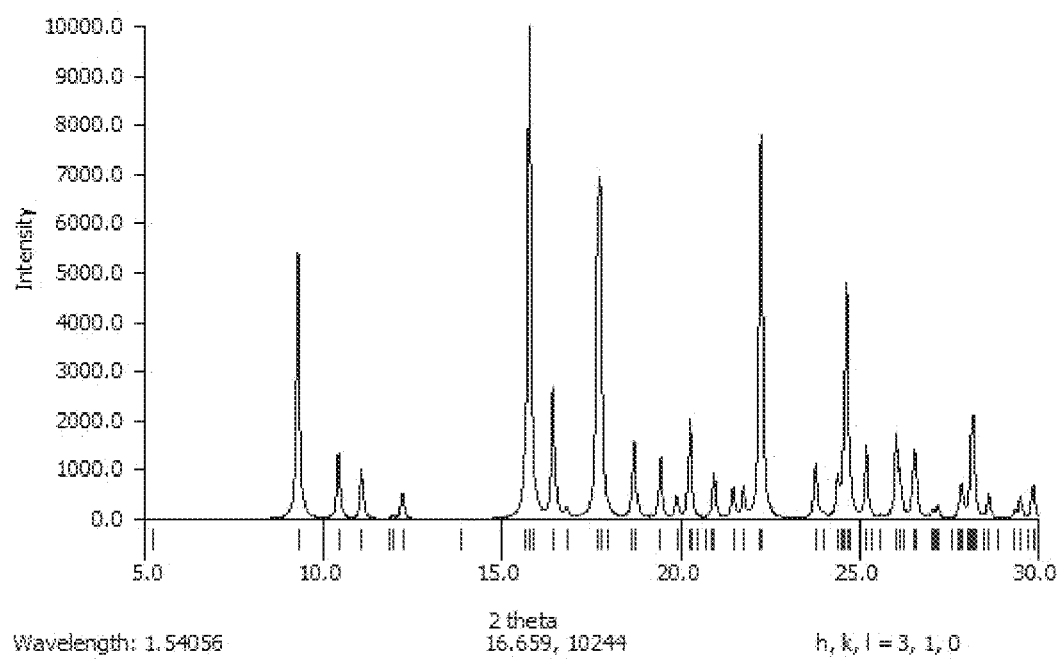
FIG. 5 shows a simulated x-ray power diffraction (XRPD) of crystalline bis-miprocin fumarate from its single crystal data.

FIG. 5. Is a simulated x-ray power diffraction (XRPD) of crystalline bis-miprocin fumarate from its single crystal data. Crystalline bis-miprocin fumarate may be characterized by the peaks at 9.3, 15.8, and 16.4° 2θ±0.2° 2θ as well as by an XRPD pattern substantially similar to FIG. 5.

REFERENCES

Bruker (2016). APEX3, SAINT, and SADABS. Bruker AXS Inc., Madison, Wis., USA.
Cameron, L. P., Nazarian, A. & Olson, D. E. (2020). J. Psychoactive Drugs.
Carhart-Harris, R. L. & Goodwin, G. M. (2017). Neuropsychopharmacology, 42, 2105-2113.
Chadeayne, A. R., Pham, D. N. K., Golen, J. A. & Manke, D. R. (2019a). Acta Cryst. E75, 1316-1320.
Dolomanov, O. V., Bourhis, L. J., Gildea, R. J., Howard, J. A. K. & Puschmann, H. (2009). J. Appl. Cryst. 42, 339-341.
Etter, M. C., MacDonald, J. C. & Bernstein, J. (1990). Acta Cryst. B46, 256-262.
Johnson, M. W. & Griffiths, R. R. (2017). Neurotherapeutics 14, 734-740.
Klein, A. K., Chatha, M., Laskowski, L. J., Anderson, E. I., Brandt, S. D., Chapman, S. J., McCorvy, J. D., & Halberstadt, A. L., Investigation of the Structure—Activity Relationships of Psilocybin Analogues (2020). ACS Pharmacol. Transl. Sci.
Repke, D. B., Ferguson, W. J. & Bates, D. K. (1981). J. Heterocycl. Chem. 18, 175-179.
Repke, D. B., Grotjahn, D. B. & Shulgin, A. T. (1985). J. Med. Chem. 28, 892-896.
Sheldrick, G. M. (2015). Acta Cryst. C71, 3-8.

The invention claimed is:

1. A method of treating a brain disorder, the method comprising the step of:
    administering to a subject in need thereof a therapeutically effective amount of crystalline bis(4-hydroxy-N-methyl-N-isopropyltryptammonium) fumarate.

2. The method of claim 1, wherein the brain disorder is selected from the group consisting of Huntington's disease, Alzheimer's disease, dementia, and Parkinson's disease.

3. A method of treating a disorder selected from the group consisting of: a developmental disorder; delirium; an amnestic disorder; a cognitive disorder; a psychiatric disorder due to a somatic condition; a drug-related disorder; a mood disorder; an anxiety disorder; a somatoform disorder; a factitious disorder; a dissociative disorder; an eating disorder; a sleep disorder; an impulse control disorder; an adjustment disorder; and a personality disorder, the method comprising the step of:
    administering to a subject in need thereof a therapeutically effective amount of crystalline bis(4-hydroxy-N-methyl-N-isopropyltryptammonium) fumarate.

4. The method of claim 3, wherein the disorder is a developmental disorder.

5. The method of claim 3, wherein the disorder is delirium.

6. The method of claim 3, wherein the disorder is an amnestic disorder.

7. The method of claim 3, wherein the disorder is a cognitive disorder.

8. The method of claim 3, wherein the disorder is a psychiatric disorder due to a somatic condition.

9. The method of claim 3, wherein the disorder is a drug-related disorder.

10. The method of claim 3, wherein the disorder is a mood disorder.

11. The method of claim 3, wherein the disorder is an anxiety disorder.

12. The method of claim 3, wherein the disorder is a somatoform disorder.

13. The method of claim 3, wherein the disorder is a factitious disorder.

14. The method of claim 3, wherein the disorder is a dissociative disorder.

15. The method of claim 3, wherein the disorder is an eating disorder.

16. The method of claim 3, wherein the disorder is a sleep disorder.

17. The method of claim 3, wherein the disorder is an impulse control disorder.

18. The method of claim 3, wherein the disorder is an adjustment disorder.

19. The method of claim 3, wherein the disorder is a personality disorder.

20. The method of claim 1, wherein the crystalline bis(4-hydroxy-N-methyl-N-isopropyltryptammonium) fumarate is characterized by:
   a monoclinic, C2lc crystal system space group at a temperature of about 200 K;
   unit cell dimensions a=19.770 (13) Å, b=9.477 (6) Å, c=17.620 (12) Å, and β=105.78 (2°),
   an XRPD having peaks at 9.3, 15.8, and 16.4° 2θ+0.2°2θ, or
   an XRPD pattern substantially similar to FIG. 5.

21. The method of claim 3, wherein the crystalline bis(4-hydroxy-N-methyl-N-isopropyltryptammonium) fumarate is characterized by:
   a monoclinic, C2lc crystal system space group at a temperature of about 200 K;
   unit cell dimensions a=19.770 (13) Å, b=9.477 (6) Å, c=17.620 (12) Å, and β=105.78 (2°),
   an XRPD having peaks at 9.3, 15.8, and 16.4° 2θ+0.2°2θ, or
   an XRPD pattern substantially similar to FIG. 5.

\* \* \* \* \*